(12) United States Patent
Hung

(10) Patent No.: US 8,282,640 B2
(45) Date of Patent: Oct. 9, 2012

(54) SINOLIFT RIDGE EXPANSION OSTEOTOME

(76) Inventor: William Y. S. Hung, Rancho Cucamonga, CA (US)

( * ) Notice: Subject to any disclaimer, the term of this patent is extended or adjusted under 35 U.S.C. 154(b) by 993 days.

(21) Appl. No.: 12/154,518

(22) Filed: May 23, 2008

(65) Prior Publication Data

US 2009/0292288 A1    Nov. 26, 2009

(51) Int. Cl.
*A61B 17/00* (2006.01)

(52) U.S. Cl. .......................................... 606/84

(58) Field of Classification Search ............... 606/79–85
See application file for complete search history.

(56) References Cited

U.S. PATENT DOCUMENTS 5,891,149 A * 4/1999 Young et al. ............... 606/80

* cited by examiner

*Primary Examiner* — Kevin T Truong
*Assistant Examiner* — Sameh Boles
(74) *Attorney, Agent, or Firm* — Raymond Y. Chan; David and Raymond Patent Firm

(57) ABSTRACT

The present invention provides an osteotome for sinus lifting and dental ridge expansion which includes an osteotome shank, a trepanelevation tip member, and a head. The trepanelevation tip member provides a cavity at a tip end and a prominence protruded from the bottom of the cavity. In this manner, during dental ridge expansion, the sharp edge of the trepanelevation tip member will secure the position and provide initial splitting of bones of sinus floor. Subsequently, the prominence will provide appropriate pressure for bone lifting. By applying the splitting force and compaction force alternatively in the same tip, the edge and prominence of the osteotome can lift the sinus in a much safer and more effective manner.

20 Claims, 3 Drawing Sheets

SINOLIFT RIDGE EXPANSION OSTEOTOME

BACKGROUND OF THE PRESENT INVENTION

1. Field of Invention

The present invention relates to osteotome, and more particularly to a sinolift ridge expansion osteotome for sinus lifting, dental ridge expansion and trepanelevation.

2. Description of Related Arts

One of the most common anatomical limitations in oral implantology is bone atrophy of the upper maxilla. Narrow alveolar crests make it difficult to do implant surgery. In 1994, the first cylindrical-conical expansion osteotome was developed expanding atrophic bone crests in order to secure sufficient bone width for dental implant placement. Living bone is much softer than dried bone, and can be drilled hole and stretched open, which is called bone expansion. After an area of bone has bone expansion, it allows for larger dental implants to be inserted into the bone. Since larger implants have greater area to bond to the bone and so have a better long term prognosis. Before the bone expansion procedure, a small hole is first drilled though the center of the area of the bone to be expanded. Then a series of bone expansion tools are tapped into the hole. As the bone expansion tools get progressively larger, the hole in the bone gets progressively larger and the walls expand. The hole created by the bone expansion can then be filled with bone or an implant can be immediately inserted into the hole. Bone expansion expands or widens the walls of the bone.

Currently, the frequently used tools for bone expansion are osteotomes. Generally an osteotome has an active part, a handle, and a posterior part to apply the mallet. The active part is slightly conical, and has two different shapes: Sharpened and concave. Osteotomes with sharpened tips are used to perform bone expansion and ridge splitting. Osteotomes with concave ends are used to achieve bone compactation and to make elevation of sinus via alveolar approach. However, there are disadvantages for both ends which cause some surgery failure and perforation of sinus. For example, because the sharpened tip has one contact tip at the top, sometimes the tip will slide away from the desired point on the bone when a force is exerted. This is danger to provide such an unexpected force in the narrow ridge bone area. Also, a sharpened tip can only drill into the bone but fail to compress the bone at the bottom of the sinus. The concave end also has a problem. The concave enlarge the area of the inner face, with the same force applied, the intention of the pressure is reduced. As a result, larger force must be exerted onto the osteotome to condense the bone crest, and it will be more difficult to control. While force being applied, patient can feel serious vibration throughout the whole head, skull and neck, which is very uncomfortable to patient. This often increases anxiety and scariness of patient. Also, tapping of the expansion osteotome with the surgical mallet is another process highly depends on the personal skills of the operators, which means technique sensitive. This introduces more uncertainty during a surgery.

According to study, there were millions of patients receiving dental implant surgeries annually in the past few years. Therefore, to invent an innovative osteotome is a compelling necessity in order to benefit millions of patients, who received dental implant surgeries.

SUMMARY OF THE PRESENT INVENTION

An object of the present invention is to provide a sinolift ridge expansion osteotome which is stable and non-slippery.

Another object of the present invention is to provide a sinolift ridge expansion osteotome which can reduce vibration and improve patient's comfort.

Another object of the present invention is to provide a sinolift ridge expansion osteotome which is reliable and easy to use.

Another object of the present invention is to provide a sinolift ridge expansion osteotome wherein the tip of the osteotome can be located on the desired position of the bone securely and reduce the risk of maxillary sinus perforation.

Another object of the present invention is to provide a sinolift ridge expansion osteotome wherein the tip of the osteotome can provide less pressure for sinus lift efficiently.

Another object of the present invention is to provide a sinolift ridge expansion osteotome which can lift sinus safely and reduce the risk of perforation of sinus and the risk of infection/bleeding.

Another object of the present invention is to provide a sinolift ridge expansion osteotome which can direct impact force from the surgical mallet axially.

Another object of the present invention is to provide a sinolift ridge expansion osteotome which can absorb the harmful impact and excessive force when apply a surgical mallet whereon.

Another object of the present invention is to provide a sinolift ridge expansion osteotome which produces less noise and vibration when apply a surgical mallet whereon that can improve patient's comfort.

Another object of the present invention is to provide a sinolift ridge expansion osteotome which can direct impact force from the surgical mallet axially in multiple directions, including vertical, lateral and oblique force.

Accordingly, in order to accomplish the above objects, the present invention provides a sinolift ridge expansion osteotome, comprising:

an osteotome shaft having a first end and a second end;

a trepanelevation tip member extending from the first end, wherein the trepanelevation tip member has a concave tip formed at a tip end thereof, the concave tip having a concave bottom and a concave wall readially and outwardly extended to a periphery edge of the trepanelevation tip member to form a sharpen tip edge of the concave tip and define a cavity at the tip end of the trepanelevation tip member, the trepanelevation tip member further providing at least a prominence protruded from the concave bottom having a height at least equal to or less than a depth of the concave tip; and a head providing at the second end of the osteotome.

These and other objectives, features, and advantages of the present invention will become apparent from the following detailed description, the accompanying drawings, and the appended claims.

DETAILED DESCRIPTION OF THE PREFERRED EMBODIMENT

Figure 1:
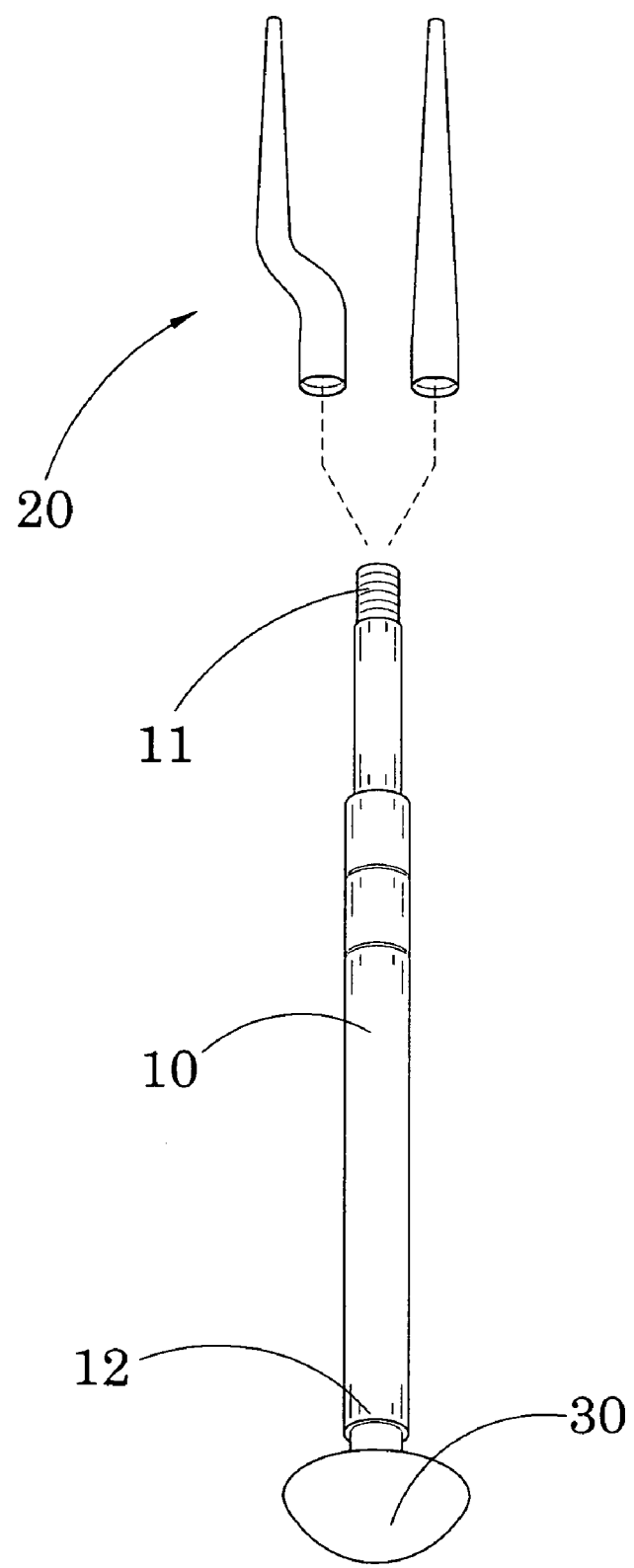
FIG. 1 is a perspective view of the sinolift ridge expansion osteotome.
Figure 2:
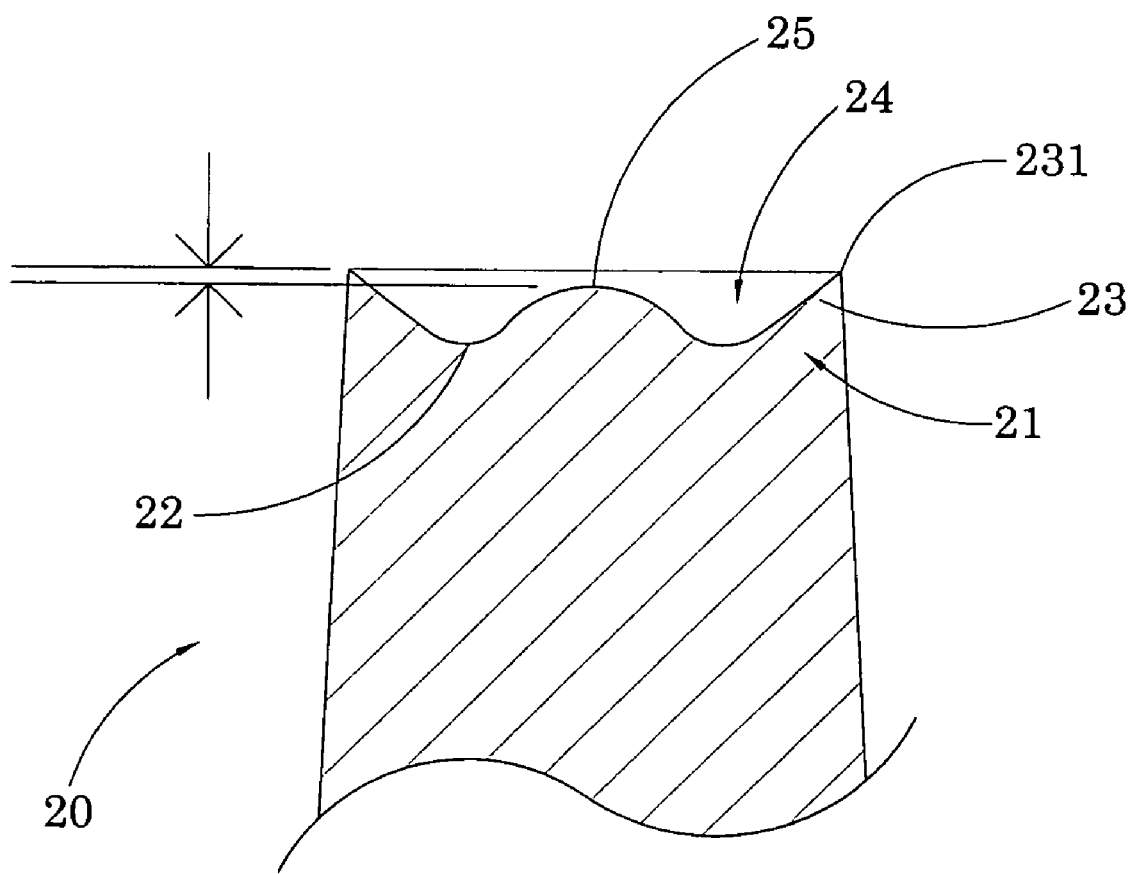
FIG. 2 is a longitudinal sectional view of the trepanelevation tip member of the sinolift ridge expansion osteotome.
Figure 3:
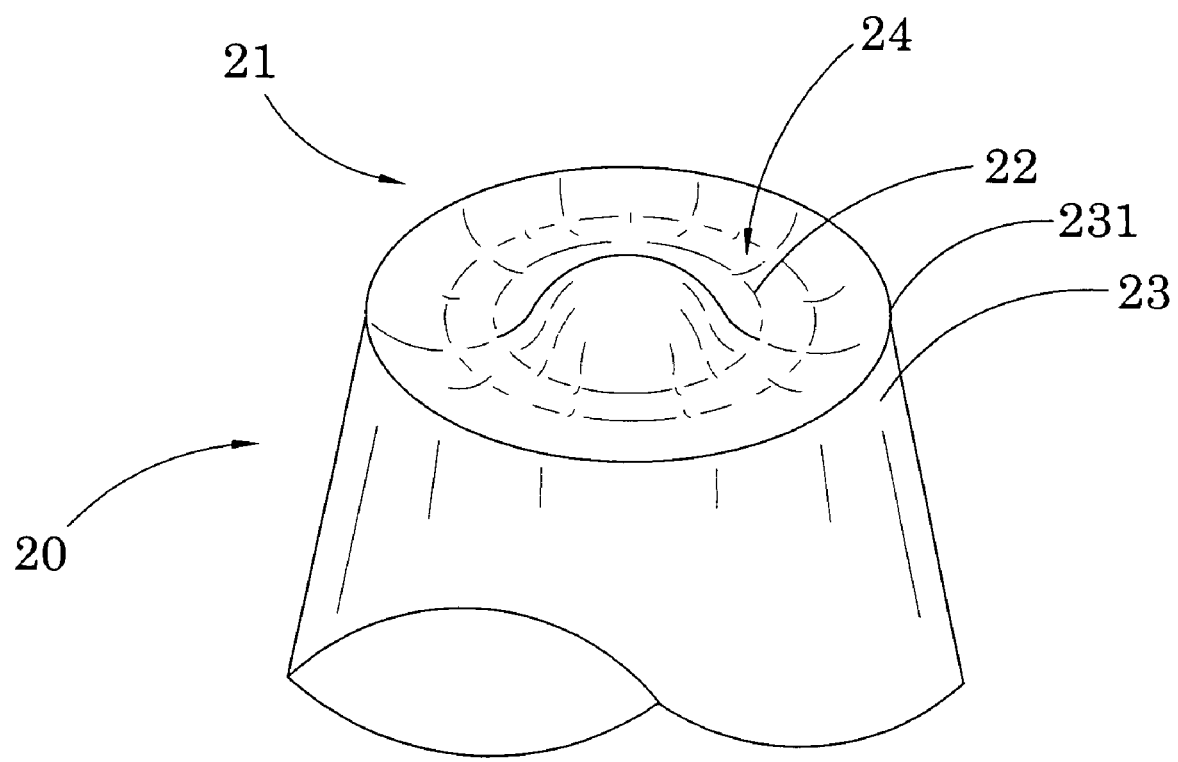
FIG. 3 is a perspective view of the trepanelevation tip member of the sinolift ridge expansion osteotome.

Referring to the FIGS. 1 to 3 of the drawings, the present invention provides a sinolift ridge expansion osteotome for sinus lifting, dental ridge expansion and trepanelevation, wherein the sinolift is a kind of trepan-like elevation. The sinolift ridge expansion osteotome comprises an osteotome shank 10, a trepanelevation tip member 20 and a head 30.

The osteotome shank 10 is an elongated body having a first end 11 and a second end 12. The trepanelevation tip member 20 is securely connected to the first end 11 and the head 30 is securely connected with the second end 12 according to the preferred embodiment as shown in FIG. 1. Alternatively, the trepan elevation tip 20 and/or the head 30 can be integrally made at two ends of the osteotome shank 10.

The osteotome shank 10 is adapted for the operator to hold, position the trepanelevation tip member 20 onto desired location of the crest bone, and secure the position and provide initial splitting of bones of sinus floor. For better holding by hand, some portion of the osteotome shank 10 has a roughed surface to increase friction. The cross section of the column can also be made into polygon, in this way the hand of the operator can control the rotation of the osteotome shank 10. Referring to FIG. 1, since the osteotome is operated in oral cavity which has limited space, the osteotome shank 10 is cranked at the top portion, so that the trepanelevation tip member 20 can be extended into the oral cavity with a right angle, while the rest portion of the osteotome can be held by hand outside the oral cavity.

The trepanelevation tip member 20 is extended from the first end 11 of the osteotome shank 10. In a preferred embodiment of the present invention, the trepanelevation tip member 20 has a circular cross section having the same diameter. In an alternative mode, the trepanelevation tip member 20 is in taper shape that reduces the diameter thereof gradually. It is appreciated that the cross section of the cylinder can be made in different shapes, such as polygon or ellipse.

Referring to FIGS. 2 and 3, the trepanelevation tip member 20 has a concave tip 21 formed at a tip end thereof, which has a concave bottom 22 and a concave wall 23 radially and outwardly extended to a periphery edge of the trepanelevation tip member 20 to form a sharpen tip edge 231 of the concave tip 21. In an embodiment of the present invention, the concave wall 23 extended from the concave bottom 22 forms a smooth curvature. The concave bottom 22 can be made to have a curve surface or a flat surface.

The concave bottom 22 and the concave wall 23 integrally define a cavity 24 at the tip end of the trepanelevation tip member 20. It is worth mentioning that the sharpen tip edge 231 is the highest tip of the tip end as shown in FIG. 2 to ensure that when the trepanelevation tip member 20 to be positioned on a surface of a bone, the sharpen tip edge 231 can be stick into the bone so as to secure the position of the trepanelevation tip member 20.

Referring to FIGS. 2 and 3, the trepanelevation tip member 20 also provides a prominence 25 protruded from the concave bottom 22 to provide appropriate pressure for bone lifting. In a preferred embodiment of the present invention, the prominence 25 is protruded from a central portion of the concave bottom 22. The prominence 25 has a convex shape and a smoothly curved exterior surface. The height of the prominence 25 must be equal or less than the depth of the concave tip 21, so that the prominence 25 does not extend beyond the sharpen tip edge 231. In this manner, the prominence 25 will not be the first portion contacting with the surface of the bone, in order to prevent the trepanelevation tip member 20 from sliding away from the desired position.

When the trepanelevation tip member 20 is applied on the surface of the bone, the sharpen tip edge 231 first sticks into the bone and secures its position. By tapping a surgical mallet (not shown in Figures) on the head 30 of the osteotome, the trepanelevation tip member 20 will perform the bone expansion with the outer wall. At the same time, the trepanelevation tip member 20 is going deeper into the sinus and elevates the sinus floor. Because the trepanelevation tip member 20 has the convex prominence 25, the intention of the pressure is enlarged. This will increase the efficiency to compress the bone material inside the cavity 24 of the trepanelevation tip member 20. As the sinus is getting deeper, and the bone wall is getting denser, it is easier to perform the dental implant later. It is worth mentioning that by applying the splitting force and compaction force alternatively in a same tip, the edge and the prominence 25 of the osteotome can lift the sinus in a much safer and more effective manner.

In an alternative embodiment of the present invention, the trepanelevation tip members 20 are replaceable. So one osteotome shank 10 can adapt to different trepanelevation tip members 20 with different sizes and styles. The dimension of the trepanelevation tip member 20 is various according to the process of the ridge expansion. The rate between the size of the prominence 25 and the concave tip 21 is also various according to different purposes. In a preferred embodiment, the sharpen tip edge 231 is a circular edge having a diameter of 0.5~0.6 mm and that the diameter of the prominence 25 is 0.2~0.3 mm.

It is appreciated that the trepanelevation tip member 20 may have more than one prominence 25 and the prominence may also have alternative shapes, for example, the shape of a hemisphere, or the shape of a pyramid.

Referring to FIG. 1, the head 30 of the osteotome of the present invention is integrally connected with the second end 12 of the osteotome shank 10 by a mechanical manner such as screwing for application of surgical mallet (not shown in the drawings). The head 30 can be made of non-metal material such as rubber, plastic, and wood. Such soft material enables a mallet to be applied on the head of the osteotome with no loud sound being produced like metal does that may cause uncomfortable feeling to the patients. Since dental ridge expansion is operated in oral cavity which is close to the hearing system, it is very important to reduce the noise. Also, these types of material are elastic which can absorb a portion of the impact and vibration when a mallet hits on it. The bone is bristle that, if too much impact is applied to the crest bone, it will be broken or split and make the implant very difficult. Also, the impact will be transferred to the brain through the bone. It is harmful if the impact force is too large. The capability of utilizing the elastic head 30 according to the present invention can diminish the risk of breaking the bone and reduce the possible injure to the brain.

The head 30 can be shaped in a sphere or a hemisphere. In a preferred embodiment, the head 30 of the osteotome is embodied as an enlarged mushroom-like shape. In this manner, if the force exerted by the mallet is not parallel to the axial of the trepanelevation tip member 20, the elastic head will absorb the lateral force, and transfer the longitudinal force to the osteotome shank 10.

One skilled in the art will understand that the embodiment of the present invention as shown in the drawings and described above is exemplary only and not intended to be limiting. It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A sinolift ridge expansion osteotome for dental ridge expansion, comprising:

an osteotome shaft having a first end and a second end;

a trepanelevation tip member extending from said first end of said osteotome shaft, said trepanelevation tip member having a taper shape that gradually reduces a diameter to a tip end such that the diameter of said tip end is smaller than said first end of said osteotome shaft for enabling said tip end locating within an oral cavity, said trepanelevation tip member having a concave tip formed at said tip end thereof, said concave tip having a concave bottom and a concave wall extended to a periphery edge of said trepanelevation tip member to form a sharpen tip edge of said concave tip and define a cavity at said tip end of said trepanelevation tip member, said trepanelevation tip member further providing at least a prominence which is protruded from a central portion of said concave bottom and has a height at least equal to or less than a depth of said concave tip, wherein said concave bottom is extended between said prominence and said concave wall, wherein said concave bottom and said concave wall integrally form said cavity around said prominence; and a head providing at said second end of the osteotome shaft for being located out of the oral cavity, wherein said head receives an impact force and longitudinally transmits the impact force to said osteotome shaft toward said sharpen tip edge of said trepanelevation tip member, wherein said sharpen tip edge is higher than said prominence and forms a highest tip of said tip end, such that when said trepanelevation tip member is positioned on a surface of a bone within the oral cavity, said sharpen tip edge is able to be stick into the bone so as to secure the position of said trepanelevation tip member, wherein said concave bottom and said concave wall radially and outwardly extended to said periphery edge of said trepanelevation tip member to form said sharpen tip edge of said concave tip, said concave wall is extended from the concave bottom to form a smooth curvature.

2. The osteotome, as recited in claim 1, wherein said trepanelevation tip member is securely connected to said first end and said head is securely connected with said second end.

3. The osteotome, as recited in claim 2, wherein said concave bottom is a curved surface extended between said prominence and said concave wall.

4. The osteotome, as recited in claim 3, wherein said prominence has a convex shape and a smoothly curved exterior surface, such that said prominence is prevented from being a first portion contacting with the surface of the bone within the oral cavity so as to prevent said trepanelevation tip member from sliding away from a desired position.

5. The osteotome, as recited in claim 2, wherein said concave bottom is a flat surface extended between said prominence and said concave wall.

6. The osteotome, as recited in claim 5, wherein said prominence has a convex shape and a smoothly curved exterior surface, such that said prominence is prevented from being a first portion contacting with the surface of the bone within the oral cavity so as to prevent said trepanelevation tip member from sliding away from a desired position.

7. The osteotome, as recited in claim 2, wherein said sharpen tip edge is a circular edge having a diameter of approximately 0.5 mm to 0.6 mm and that a diameter of said prominence is approximately 0.2 mm to 0.3 mM.

8. The osteotome, as recited in claim 1, wherein said trepanelevation tip member is replaceable connected to said first end and said head is securely connected with said second end.

9. The osteotome, as recited in claim 8, wherein said concave bottom is a curved surface extended between said prominence and said concave wall.

10. The osteotome, as recited in claim 9, wherein said prominence has a convex shape and a smoothly curved exterior surface, such that said prominence is prevented from being a first portion contacting with the surface of the bone within the oral cavity so as to prevent said trepanelevation tip member from sliding away from a desired position.

11. The osteotome, as recited in claim 8, wherein said concave bottom is a flat surface extended between said prominence and said concave wall.

12. The osteotome, as recited in claim 11, wherein said prominence has a convex shape and a smoothly curved exterior surface, such that said prominence is prevented from being a first portion contacting with the surface of the bone within the oral cavity so as to prevent said trepanelevation tip member from sliding away from a desired position.

13. The osteotome, as recited in claim 12, wherein said sharpen tip edge is a circular edge having a diameter of approximately 0.5 mm to 0.6 mm and that a diameter of said prominence is approximately 0.2 mm to 0.3 mM.

14. The osteotome, as recited in claim 13 wherein said head is made of elastic material for absorbing a portion of impact and vibration when a mallet hits thereon so as to minimize noise generated at said head when said tip end of said trepanelevation tip member impacts the surface of the bone within the oral cavity, wherein said head is formed in hemispherical shape that said head absorbs said impact force at lateral direction and transfers said impact force at longitudinal direction to said osteotome shaft.

15. The osteotome, as recited in claim 12, wherein said head is made of elastic material for absorbing a portion of impact and vibration when a mallet hits thereon so as to minimize noise generated at said head when said tip end of said trepanelevation tip member impacts the surface of the bone within the oral cavity, wherein said head is formed in hemispherical shape that said head absorbs said impact force at lateral direction and transfers said impact force at longitudinal direction to said osteotome shaft.

16. The osteotome, as recited in claim 11, wherein said sharpen tip edge is a circular edge having a diameter of approximately 0.5 mm to 0.6 mm and that a diameter of said prominence is approximately 0.2 mm to 0.3 mM.

17. The osteotome, as recited in claim 11, wherein said head is made of elastic material for absorbing a portion of impact and vibration when a mallet hits thereon so as to minimize noise generated at said head when said tip end of said trepanelevation tip member impacts the surface of the bone within the oral cavity, wherein said head is formed in hemispherical shape that said head absorbs said impact force at lateral direction and transfers said impact force at longitudinal direction to said osteotome shaft.

18. The osteotome, as recited in claim 1, wherein said concave bottom is a curved surface extended between said prominence and said concave wall.

19. The osteotome, as recited in claim 18, wherein said sharpen tip edge is a circular edge having a diameter of approximately 0.5 mm to 0.6 mm and that a diameter of said prominence is approximately 0.2 mm to 0.3 mM.

20. The osteotome, as recited in claim 18, wherein said head is made of elastic material for absorbing a portion of impact and vibration when a mallet hits thereon so as to minimize noise generated at said head when said tip end of said trepanelevation tip member impacts the surface of the bone within the oral cavity, wherein said head is formed in hemispherical shape that said head absorbs said impact force at lateral direction and transfers said impact force at longitudinal direction to said osteotome shaft.

* * * * *